United States Patent
Radley

(10) Patent No.: US 8,660,239 B2
(45) Date of Patent: Feb. 25, 2014

(54) DETECTOR APPARATUS AND METHOD

(75) Inventor: Ian Radley, Bishop Auckland Durham (GB)

(73) Assignee: Kromek Limited, Sedgefield, County Durham (GB)

( * ) Notice: Subject to any disclaimer, the term of this patent is extended or adjusted under 35 U.S.C. 154(b) by 331 days.

(21) Appl. No.: 13/126,409

(22) PCT Filed: Nov. 16, 2009

(86) PCT No.: PCT/GB2009/051541
§ 371 (c)(1),
(2), (4) Date: May 31, 2011

(87) PCT Pub. No.: WO2010/058201
PCT Pub. Date: May 27, 2010

(65) Prior Publication Data
US 2011/0222658 A1    Sep. 15, 2011

(30) Foreign Application Priority Data
Nov. 18, 2008   (GB) .................................. 0821050.2

(51) Int. Cl.
*G21K 5/10*    (2006.01)
(52) U.S. Cl.
USPC .............................. 378/146; 378/116; 378/51
(58) Field of Classification Search
USPC .................... 378/51, 53, 55, 57, 62, 146, 116
See application file for complete search history.

(56) References Cited

U.S. PATENT DOCUMENTS

| 4,686,695 | A | | 8/1987 | Macovski |
| 5,490,197 | A | * | 2/1996 | Albert et al. ................... 378/113 |
| 5,572,037 | A | * | 11/1996 | Liu et al. .................... 250/483.1 |
| 5,943,388 | A | | 8/1999 | Tumer |
| 6,081,582 | A | | 6/2000 | Mazess et al. |
| 2005/0002486 | A1 | | 1/2005 | Maschke |

FOREIGN PATENT DOCUMENTS

EP   1 227 316    7/2002
WO   WO 96/24047   8/1996

OTHER PUBLICATIONS

International Search Report, dated Dec. 17, 2010.
Written Opinion, dated Dec. 17, 2010.

* cited by examiner

*Primary Examiner* — Jurie Yun
(74) *Attorney, Agent, or Firm* — Drinker Biddle & Reath LLP

(57) ABSTRACT

A detector apparatus is described for scanning of and obtaining radiation data from an object and generating an image therefrom. The apparatus comprises a radiation detector system spaced therefrom to define a scanning zone and to collect a dataset of information about radiation incident at the detector after interaction with an object and to resolve collected information spatially in two dimensions across a scan area and spectroscopically across a plurality of frequency bands in the spectrum of the source. A detector exhibits a spectroscopically variable response across at least a part of the spectrum of the source and to resolve collected information spatially with a rastering module configured to divide the scanning area into a plurality of pixels two dimensions; and a control to move the detector to scan such pixels successively and thereby collect a dataset for each pixel. A method is also described.

26 Claims, 2 Drawing Sheets

US 8,660,239 B2

DETECTOR APPARATUS AND METHOD

FIELD OF THE INVENTION

This invention relates to a detector apparatus and method for the inspection and characterisation of material in three-dimensional space.

The invention in particular preferably relates to an apparatus and method making use of high energy radiation such as x-rays or gamma-rays to scan objects and generate spatially resolved information about their contents and/or composition based on radiation received at a detector after interaction with the object, and preferably to generate an image therefrom. The invention in particular preferably relates to the measurement of transmitted intensity to gain information about the internal contents and/or composition of objects. The invention in a preferred case relates in particular to a detector apparatus and method for the production of a two-dimensional image, but is not limited to such imaging.

This scanning principle is widely employed for example, without limitation, in medical imaging, imaging for quality control purposes or the purposes of determining the integrity of the structure, security scanning or the like.

BACKGROUND

X-Ray absorption in particular has been used as the basis for systems for scanning objects to create some form of representational image of the contents or components thereof. The thicker or more dense an object is then the more it will attenuate an x-ray beam. By use of suitable detectors and a suitable source, radiographs of an item under screening in the form of images based on the absorption of an object or set of objects can be generated.

Typically, an x-ray source generates an essentially two-dimensional beam and detectors of transmitted x-rays in one or two dimensional array are used to resolve transmitted information spatially into two dimensions based on transmitted x-rays (and hence differentiating by absorption). A computer is used to generate a two-dimensional image of the object from this spatially resolved information. In a refinement, it is known to build up successive two-dimensional image slices in cross-section and display these successively. Such a principle is employed in CAT scanning for example. Similar principles can be applied to imaging based on other interactions of source and object, for example based on back-scattered radiation.

These known apparatus and methods tend to give limited information about the material content. In essence, at its simplest, all that is being measured is transmissivity of the object to the source radiation. Conventional detectors merely collect amplitude information discriminated spatially, but do not discriminate transmitted radiation spectroscopically.

However, it is known that spectroscopic information from transmitted x-rays could be used to give additional information about the material content of the objects or components being scanned. It is known that the x-ray absorption properties of any material can vary spectroscopically, and that the amount by which the absorption properties vary depends in particular on atomic number. Silicon-based dual band energy detectors have been used to generate pairs of images as low and high energy allowing some spectroscopic discrimination.

Recent development of detector materials that can resolve spectroscopic information about the transmitted X-rays more effectively has led to the development of apparatus that discriminate across a larger range of bands and generate a larger plurality of spectroscopically differentiated images. For example U.S. Pat. No. 5,943,388 describes a system that makes use of cadmium telluride detectors to image across at least three energy bands and generate at least three images. Such systems better exploit the effect of differential spectral absorption by different materials and enable a better approximation to be made between transmissivity and composition. However, the detector materials are expensive and difficult to fabricate, particularly if configured as a linear or area array with high pixel resolution.

SUMMARY OF THE INVENTION

It is an object of the present invention to mitigate some or all of the above disadvantages of prior art scanning systems and methods.

It is a particular preferred object of the present invention to provide an apparatus and method for scanning and preferably further for imaging of objects, that makes effective and practical use of resolution of radiation produced by interaction of a scanned object both spatially and spectroscopically.

Therefore, according to one aspect of the invention there is provided a detector apparatus for scanning of and obtaining radiation data from, and preferably an image of, an object comprising:

a radiation source;
a radiation detector system spaced therefrom to define a scanning zone and to collect in use a dataset of information about radiation incident at the detector after interaction with an object in the scanning zone and adapted to resolve such collected information spatially in two dimensions across a scan area and spectroscopically across a plurality of frequency bands in the spectrum of the source;
wherein the detector system is adapted to resolve such collected information spectroscopically in that it comprises a detector that exhibits a spectroscopically variable response across at least a part of the spectrum of the source; and
wherein the detector system is adapted to resolve such collected information spatially in that it comprises:
a rastering module configured to divide the scanning area into a plurality of pixels in each of two dimensions;
a detector control means to move the detector across the scanning area to scan such pixels successively and thereby collect a dataset for each pixel.

The apparatus is distinctly characterised from many conventional x-ray scanning and imaging systems in two particular ways.

First, a detector is used which exhibits a spectroscopically variably response across at least a part of the spectrum of the source, and preferably at least a major part of the spectrum of the source, the apparatus then being adapted, for example by provision of suitable data processing means, to resolve radiation information collected at the detector spectroscopically across a plurality frequency bands. Preferably, the detector is adapted to resolve such collected information spectroscopically across at least three frequency bands. Conveniently, it achieves this in that it is fabricated from a material inherently capable of exhibiting a spectroscopically variable response across at least part of the spectrum of the source.

This spectroscopic resolution offers potentially significant advantages over prior art systems comprising simple detectors without energy resolution, and in the case of the preferred embodiment where radiation is resolved spectroscopically across at least three energies, over dual energy detectors. Single energy detectors give no information about variation in incident intensity with frequency attributable to the composition of an object. Dual energy detectors allow only very crude general approximations to be drawn. More complete spectral resolution enables data to be collected from which more specific inferences can be drawn. The use of material that resolves spectroscopically across a substantial part of the source is particularly advantageous. The detector is capable of detecting and collecting spectroscopically resolvable information about incident radiation in the sense that it is adapted to differentiate incident radiation simultaneously into plural separate energy bands across the spectrum of the source. For example, the detector exhibits a spectroscopically variable response across at least a part of the source spectrum allowing such simultaneous differentiation of incident radiation into plural energy bands.

However, such materials can be difficult to fabricate with the necessary spatial resolution. Accordingly, the invention is further characterised in that an image is built up on a raster principle by movement at least of the detector in at least two dimensions so as to collect data from a two dimensional scanning area. A scanning area is defined and a rastering module divides the scanning area into a plurality of pixels in each of two dimensions. The rastering module notionally divides the scanning area into an array of pixels extending over two dimensions in any suitable shape, for example forming a square or hexagonal array, at a desired resolution (that is, pixel size). However, the apparatus of the invention does not require the detector to exhibit this resolution across the full scanning area, nor even to have this resolution fully in either dimension. Instead, a detector which resolves substantially fewer pixels in each dimension, and which may even simply detect a single pixel at a time, and for example thereby present a substantially smaller detector area than the scan area, is caused to move in two dimensions across the scan area plane and thus collect successively information about the pixels defined by the rastering module until such time as a complete dataset has been built up of information for each pixel.

The system can confer two advantages in particular. First, it is not necessary for the detector to extend across the full desired scan area or to be in itself to be capable of resolving information spatially across the scan area to a desired pixel size. This can produce significant advantages in terms of practicality of fabrication and cost, particularly with materials which are used to give full spectral resolution at higher energies where achievement of fine-scale resolution by structural features alone can be complex.

Second, because the resolution is essentially a function of the rastering system and not of the detector, an apparatus can be readily switched between multiple resolutions, which can greatly enhance the flexibility of the apparatus. For example, it can be seen that the raster module could define a coarse scan of a large object in the first instance based on a relatively large notional pixel size, and a fine detail focused scan on elements or components of an object identified thereby. Preferably therefore the rastering module is configured to divide the scanning area into a plurality of pixels in each of two dimensions at a plurality of resolutions (for example, a plurality of pixel sizes), including at least a coarse and a fine resolution, and is further configured to enable selection between the plurality of resolutions, for example by a user through a suitable user input interface.

The apparatus of the invention could be included as an addition in an existing luggage/baggage/container screening system. Such an existing/established x-ray luggage screening systems such as a dual x-ray screening system could be used to identify in luggage/container suspect items that need further investigation/analysis. The apparatus of the invention could then be used for more detailed imaging of the suspect items and would offer cost advantages over known technology for detailed screening of suspect items in luggage, such as CT imaging systems.

Items of luggage/containers identified as having suspect items requiring further investigation could be passed from the established luggage/container screening system to the apparatus of the invention for detailed scanning. A coarse scan of the item of luggage/container could be carried out to identify the area for further investigation and then a fine detailed scan of the area of interest could be made. Alternatively, the area of interest for further investigation could be identified in the established luggage/container screening system and the coordinates identified and the reference coordinates passed to the apparatus of the invention by known communication means to enable a detailed scan only of the area of interest to be conducted without the need for a coarse scan.

In a preferred embodiment, the detector apparatus is configured to detect transmitted radiation for example for use in generation of a transmission radiograph in familiar manner. X-ray absorption in particular shows a resolvable functional variation that can be related to material composition, and x-ray transmission information which is resolved spectroscopically across the plurality frequency bands can exploit this. Thus, in a preferred embodiment, the apparatus comprises a radiation source and a radiation detector system space therefrom to define a scanning zone in a radiation transmission path therebetween and thus collect in use a dataset of information about transmissivity of an object in the scanning zone. However, the principles of the invention can be applied to the collection of information based on other interactions of source radiation and object.

The radiation source preferably comprises a source to deliver high-energy radiation such as ionizing radiation, for example high energy electromagnetic radiation such as x-rays and/or gamma rays, or subatomic particle radiation, and the detection system is adapted correspondingly to detect radiation in this spectrum. The radiation source for example is a broadband x-ray or gamma-ray source capable of producing broad spectrum emission over a wide range of x-ray or gamma-ray energies. Such a source will be familiar, and is widely used.

The collected transmission data is resolved spectroscopically across the plurality of frequency bands.

Optionally, the apparatus is adapted to collect in use radiation intensity data with an object in a single scanning position and for example includes a means to retain an object in a scanning position such as a receptacle into which an object can be placed. Additionally or alternatively it may include a conveyor to convey an object into and out of such scanning position.

Optionally, the apparatus is adapted to collect in use radiation intensity data with an object in a plurality of scanning positions as the object moves relative to and for example through the scanning zone, and preferably to collect in use data for an image of an object in the scanning zone, and preferably a succession of images as the object moves through the scanning zone, in that it further comprises an object handler to cause an object to move relative to and for example through the scanning zone in use.

The apparatus of the invention conveniently comprises a data processing apparatus including or constituting one or more of the rastering module, a means to resolve the collected dataset spectroscopically, means to generate a spectroscopically and spatially resolved image dataset etc.

Any suitable form of data processing apparatus combining suitable hardware and software and combining automatic and user-input steps can be envisaged. For example the apparatus of the invention comprises a suitably programmed data processing apparatus such as a suitably programmed general purpose or special purpose computer.

It will be understood that although reference is made herein for convenience to the scanning of an object this should not be considered to limit the application of the invention to the scanning of single homogenous objects. Indeed, for many envisaged applications, an "object" is likely to consist of multiple heterogeneous materials and/or to be a container or other agglomeration of multiple articles, so that any transmitted radiation path is likely to pass through multiple different materials having varied properties. One of the particular advantages of the invention is that it can facilitate resolution of such varied materials.

The key to the apparatus of the invention is that it provides a convenient means to resolve instant radiation at the detector both spatially and spectroscopically, and in particular in the preferred embodiment to build up a dataset of transmitted information resolved across two spatial dimensions and a plurality of frequencies/energies in the spectrum of the source. Such a dataset might be susceptible to a variety of uses for subsequent numerical analysis for example, in particular to use the spectroscopically resolved data to infer information concerning composition. It is not necessary in accordance with the invention for the apparatus to generate an image. As set out hereinabove, an apparatus in accordance with the invention may be used in conjunction with a conventional imaging apparatus, for example as a second level check for a suspect item identified by such conventional imaging apparatus.

However, for practical purposes it may be preferable that the apparatus in accordance with the invention itself forms part of and supplements the information offered by a scanning imaging system. In accordance with this preferred embodiment, the dataset of information collected at the detector is used to generate an image of an object in the scanning zone resolved in two dimensions in accordance with the raster pattern and resolved spectroscopically across a plurality of frequency bands within the spectrum of the source.

Optionally, the apparatus further includes an image generation apparatus to generate at least a first image from the output of the detector system; and optionally further an image display adapted to display at least the first image.

An image generation apparatus may in particular be adapted to receive datasets of intensity data from a plurality of spectroscopically resolved energy bands and display these separate datasets of intensity data as separate images successively or simultaneously to aid in object differentiation. For example spectroscopic differentiation in the collected data may be represented in a single combined image as differentiated colour, shading or marking.

The display means is conveniently a simple two dimensional display screen, for example a conventional video display screen (which term is intended to encompass any direct display or projection system exploiting any cathode ray tube, plasma display, liquid crystal display, liquid crystal on silicon display, light emitting diode display or like technology). It is a particular advantage that the method can be envisaged for use with, and the apparatus of the invention incorporated into, the standard display screens of comparable existing systems for example in the quality control, security or medical imaging fields.

For clarification it should be understood that where used herein a reference to the generation of image is a reference to the creation of information dataset, for example in the form of a suitable stored and manipulatable data file, from which a visual representation of the underlying structure of the object under investigation could be produced, for example in a suitable image data format, and references to displaying this image are references to presenting an image generated from such a dataset in a visually accessible form, for example on a suitable display means. Image encompasses a moving image.

The detector is capable of resolving the source spectrum into a plurality of energy "bands". The exact bandwidth is not directly pertinent to the invention and useful results can be obtained by any suitable approach to dividing the spectrum, either in whole or in part, into separate energy ranges. For example, the entire spectrum or a substantial part thereof may simply be divided between such a plurality of bandwidths, and each data item be considered as a measure representative of incident radiation intensity across the entire band, and for example an average intensity. Alternatively, a plurality of relatively wide bands, but with discrete gaps therebetween, may be envisaged and analysed on the same basis. Alternatively, "bands" may be narrow even to the point where they essentially approximate to an evaluation of intensity at a single energy. As used herein the concept of collected intensity at an energy "band" includes evaluation of intensity at such a discrete single energy as well as evaluation of intensity at an energy across a narrow or broad bandwidth.

Similarly the source may be a single broad spectrum source across which a plurality of bandwidths or single energies may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source may comprise an x-ray source having a relatively lower energy spectrum, for example operating below 60 keV and for example at 10 to 50 keV and one or more other sources such as radioisotope sources generating radiation at higher energies, for example above 100 keV.

A detector in accordance with the invention may simply comprise a single pixel detector (i.e., does not itself produce any spatial differentiation of incident radiation in either dimension), with the raster module enabling a full two dimensional dataset to be developed and collected via any suitable scanning pattern over time. However, the invention does not exclude the provision of a detector in which the detector itself has a differentiating resolution of a plurality of pixels in one or two directions. The requirement of the invention is that nevertheless such a composite detector is used to build up a rastered image, and will therefore in practice not be required to be configured with a structure having the desired maximum resolution of the scanning apparatus as a whole and/or not be required to have an area corresponding to the full maximum desired scan area of the apparatus as a whole. In a preferred embodiment, the detector is a single pixel detector and the apparatus builds up a two dimensional dataset entirely by the raster process.

The general principles of rastering a two-dimensional data set, for example, for the purposes of producing information presentable as an image, are well known, and the precise method by which a notional raster bitmap is built up for the scanning area, and by which this area is scanned to collect the necessary data to make up the rastered data structure, are not specifically pertinent to the invention. Typically, as will be familiar, the raster module will divide the scan area into a notional grid of pixels, and in particular to a rectangular grid, from which data will be collected by scanning, at least by moving the detector, in any suitable scan pattern which covers the whole scan area in a convenient manner. Data thus resolved into two special dimensions is stored bit for bit, pixel by pixel. Such data can for example be used to generate a pixel by pixel bitmap image data set, but in accordance with the invention data corresponding to this rastered grid pattern can also be used for none-imaging purposes. The number of bits of data which are stored for each pixel will be determined by the intended application. The special resolution of each pixel will be determined as appropriate to the application. It is an advantage of the invention that the special resolution is an artifact of the virtual pixel size created by the raster module and not of a physical pixelated resolution on the detector, and is therefore flexible.

It is necessary that the detector system is enabled to detect radiation in a manner which is spectroscopically resolvable. Preferably, a detector comprises a material that is adapted to produce spectroscopic resolution in that it exhibits a direct spectroscopic response. In particular a fabricated from a material selected to exhibit inherently as a direct material property a direct variable electrical and for example photoelectric response to different parts of the source spectrum. For example, the detector comprises a wide direct bandgap semiconductor material. For example, the detector comprises a semiconductor material or materials preferably formed as a bulk crystal, and for example as a bulk single crystal (where bulk crystal in this context indicates a thickness of at least 500 μm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_b Te$ where a and/or b may be zero.

By analogy, in accordance with a further aspect of the invention there is provided:

a method of obtaining radiation interaction data and for example transmission data from, and preferably an image of, an object comprising the steps of:

providing a radiation source such as an x-ray or gamma-ray source and a radiation detector system such as an x-ray or gamma-ray detection system spaced therefrom to define a scanning zone therebetween, wherein the detector system is adapted to resolve such collected information spectroscopically in that it comprises a detector that exhibits a spectroscopically variable response across at least a part of the spectrum of the source;

defining a scanning area for collection of radiation incident at the detector;

dividing the scanning area into a plurality of pixels in each of two dimensions;

moving the detector across the scanning area to scan such pixels successively and thereby collect a dataset for each pixel of information about radiation incident at the detector after interaction with an object in the scanning zone;

resolving each such dataset spectroscopically across a plurality of frequency bands within the spectrum of the source.

Thus, in accordance with the method, a spectroscopically resolved dataset is also developed as a dataset spatially resolved in two dimensions, with the spatial resolution attributable at least in part to a raster scanning process comprising moving at least the detector so as to perform an information collection scan across the scanning area in each of the two dimensions in an appropriate scanning pattern necessary to collect a dataset of information for each pixel.

In a preferred embodiment of the method, the detector is simply a single pixel detector, and the complete dataset is assembled by scanning each pixel individually. However, the invention admits the possibility of using a detector with some degree of resolution in one or two dimensions while the method still involves building up a rastered dataset conferring the advantage that such a detector need not be a limiting factor in the maximum resolution and/or maximum scan area of the dataset generated in accordance with the method.

The invention is not limited in its application to the scanning and/or imaging of objects moving through a scanning zone in a scanner. Information pertinent to the material composition of an object or objects in a transmission path can be obtained by a single scanning event, for example of a stationary object being scanned by a single beam of appropriate two-dimensional geometry. In such circumstance the method merely includes placing the object in a scanning zone to obtain such a single scan and single dataset of intensity data.

However, in a preferred embodiment information is collected regarding the object under test in the scanning zone in a plurality of scanning positions between which the object is translated and/or rotated. In accordance with this embodiment of the method, the method comprises the additional step of causing an object to move relative to and for example through the scanning zone as a plurality of such datasets of intensity data are collected.

In a preferred embodiment, the method comprises detection of transmitted radiation for example for use in generation of a transmission radiograph image. In this embodiment, the method comprises providing a radiation source and a radiation detector system space therefrom to define a scanning zone in a radiation transmission path therebetween, and thereby collecting a dataset of information about transmissivity of an object in the scanning zone. However, the principles of the method can be applied to the collection of information based on other interactions of source radiation and object.

The radiation source must produce a distribution of energies across a suitable spectral range for characteristic scattering, and is typically an x-ray source. Tungsten is the most appropriate target, but others could be used.

The source may be a single broad spectrum source across which a plurality of bandwidths (which term, as described above, encompasses herein single energies) may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

Preferably, the method comprises generating an image of an object in the scanning zone, and where applicable a succession of images as the object moves through the scanning zone.

In a preferred mode of operation each such image is resolved spectroscopically across a plurality of frequency bands within the spectrum of the source to generate a series of energy-differentiated images.

The method of the invention conveniently further provides the additional step of displaying such generated image or images, and in the case of multiple images might involve displaying such images simultaneously or sequentially.

In accordance with a preferred embodiment of the invention, each collected image is resolved spectroscopically across a plurality of relatively broad "imaging" bands each intended to generate an image across a broader part of the overall spectrum, so that the imaging bands together allow the generation of an energy-differentiated composite image or succession of images. The number of imaging frequency bands is conveniently between 2 and 10, and for example between 4 and 8.

Spectroscopic detectors can be operated in an energy selective manner, giving rise to the ability to present an image resolved into a significantly increased number of "imaging" energy bands compared with the two that are available from standard prior art dual energy detectors. This information can be used to improve resolvability of objects of different composition.

This is achieved in accordance with this preferred embodiment in that spectroscopic resolution of transmitted radiation in each such relatively broad band is represented in the generated image. For example, spectroscopic differentiation in the collected data is represented in the image as differentiated colour, shading or marking. A banded mapping is used in that the source spectrum is divided into a plurality of bands, for example between four and eight bands, and different colours are used to represent each such band in the displayed image. The apparatus conveniently includes suitable image processing means to effect this mapping.

An image or composite image or succession of images so generated is preferably displayed on a suitable display means.

Other preferred features of the method will be understood by analogy with the description of preferred embodiments of the apparatus and its operation.

It will be understood generally that a numerical step in the method of the invention can be implemented by a suitable set of machine readable instructions or code. These machine readable instructions may be loaded onto a general purpose computer, special purpose computer, or other programmable data processing apparatus to produce a means for implementing the numerical step specified, and in particular thereby to produce a calculation means as herein described.

These machine readable instructions may also be stored in a computer readable medium that can direct a computer or other programmable data processing apparatus to function in a particular manner, such that the instructions stored in a computer readable medium produce an article of manufacture including instruction means to implement some or all of the numerical steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the numerical steps in the method of the invention. It will be understood that a step can be implemented by, and a means of the apparatus for performing such a step composed in, any suitable combinations of special purpose hardware and/or computer instructions.

BRIEF DESCRIPTION OF THE DRAWINGS

The invention will now be described by way of example only with reference to the accompanying drawings in which.

DESCRIPTION OF THE PREFERRED EMBODIMENTS

Figure 1:
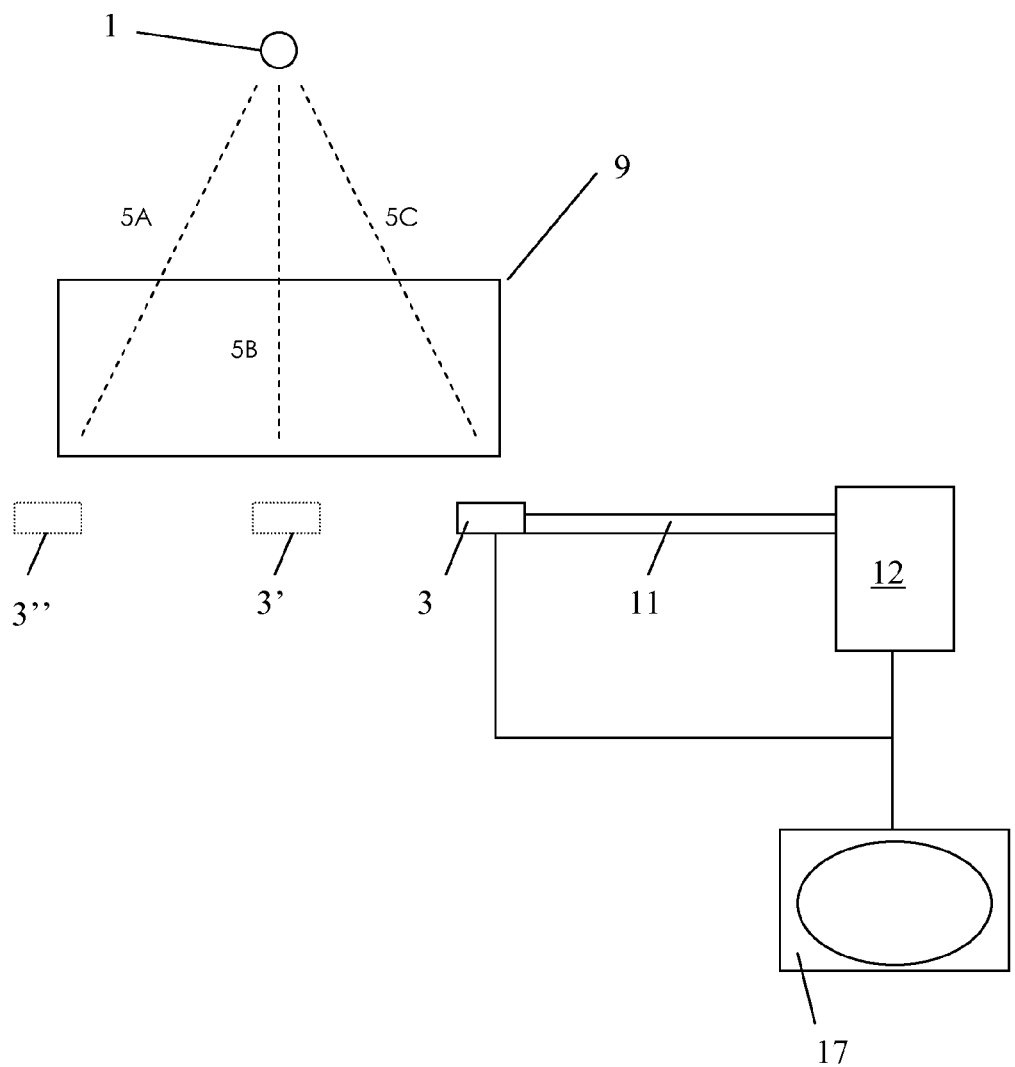
FIG. 1 is general schematic of a possible apparatus to implement an embodiment of the invention.

Referring first to the general schematic representation on FIG. 1, an x-ray source 1 and laterally spaced detector 3 together define a scanning zone Z between them. The apparatus is configured to detect transmitted x-rays and measure attenuation by absorption. In use, an object to be scanned is brought into and through or placed in the scanning zone in the usual manner, for example on a suitable conveyor belt (not shown).

In the illustrated example, a sample of material 9 sits in the scanning zone Z. An incident beam 5 from the x-ray source is illustrated. This is received at the detector 3. The source is adapted to emit an x-ray beam over a wide area. For the purpose of illustration only, three example beam directions are shown representing this area, respectively 5A, 5B and 5C. The detector in the embodiment is a reduced area detector (that is, it covers and differentiates across only a small part of the overall area to be scanned at any given time), and for example resolves to a single pixel only. In the particular illustration, the detector 3 is illustrated in position to collect transmission data from ray path 5C. As part of the raster scanning process, the detector 3 is moved to positions 3', 3" to collect data respectively from ray paths 5B and 5A by means of the actuator arm 11 under control of a control means 12.

Figure 2:
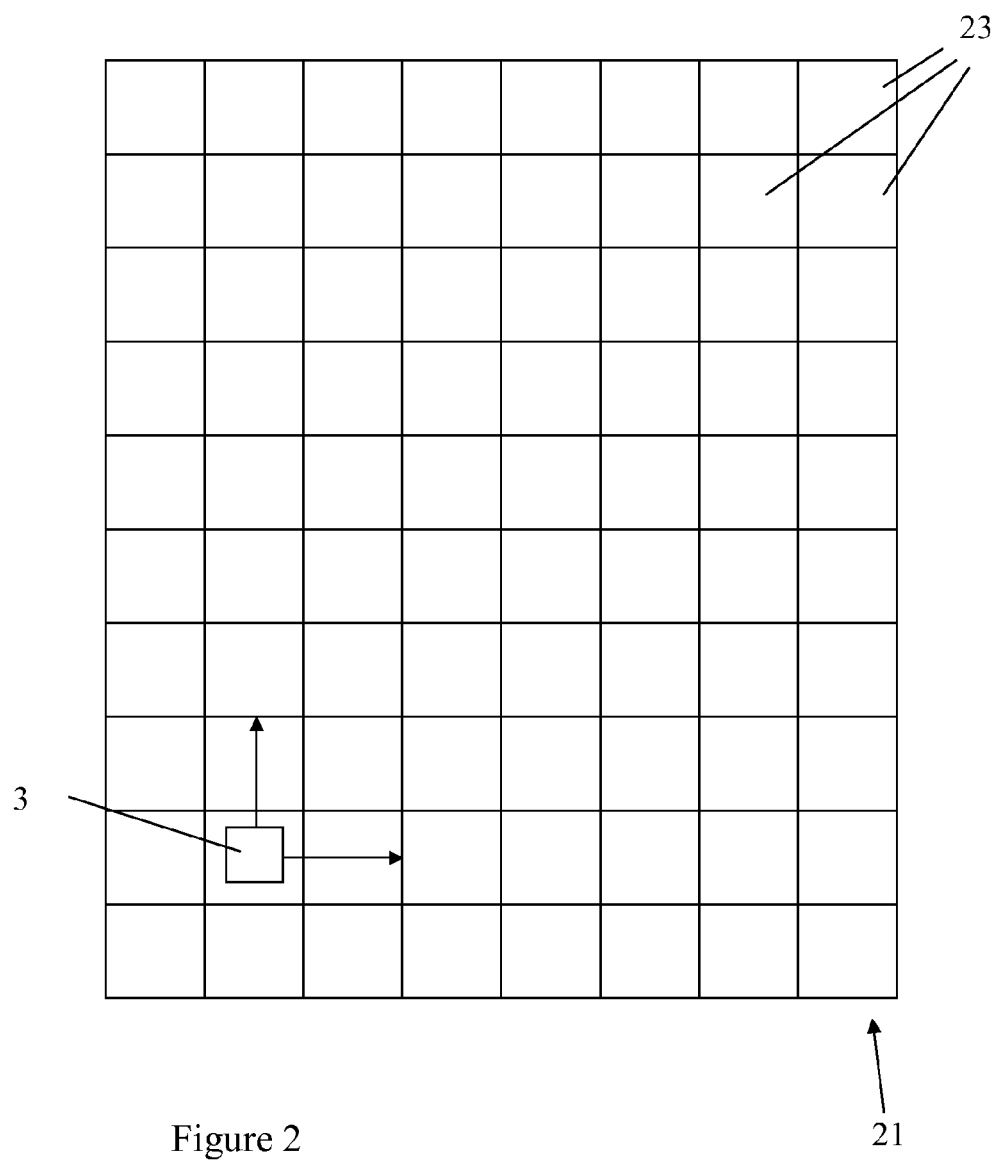
FIG. 2 illustrates a typical raster pattern to implement an embodiment of the invention.

The principles of operation of the control means can be understood with reference to FIG. 2. A raster module within the control means 12 divides a notional imaging area 21 into a plurality of pixels 23 in each of two dimensions. Under control of the control means the detector 3 is moved relatively to the object so as to effect a scan across this area in the direction of the arrows shown. In a simple embodiment, the detector is moved relative to a stationary object and source, but it will be appreciated that any arrangement effecting the necessary relative movement between the rastered image scan area and the detector to enable a scan across the whole image area and to enable a collection of data for each pixel will be sufficient to allow the invention to operate.

The precise scanning mode is not directly pertinent to the invention. For example, the image area may be scanned via a simple progressive scan, or via some more complex interlaced scan.

The size and pattern of the pixels 23 is a virtual artefact of the rastering process and is determined by the rastering module. In the embodiment, a single pixel detector is used. The spatial resolution of the scan is therefore determined entirely by the virtual resolution created by the raster. In this way, the resolution can be varied between scans for the same apparatus, in that the raster module varies the virtual pixel size 23. A user is enabled to select a desired resolution at the penalty of scan rate. A user might for example select a coarse resolution for an initial scan, and a finer scale resolution for further investigation.

Data collected at the detector 3 as it is moved to cover the rastered scan area is passed via a suitable data link to the data processing module 12. The data processing module additionally resolves the information spectroscopically, preferably across at least three separate energy bands. Thus, for each pixel a data set is generated of received intensity data which is spectroscopically resolved. Thus, the overall data set includes both spatial and spectroscopic resolution built up by a simple, effectively one-dimensional detector.

In particular, this resolved information is used to generate an image comprising both spatial and spectroscopically resolved information. For example, spatial resolution is represented in two dimensions graphically on the image. Spectroscopic resolution is represented in the image, for example as intensity, with each image being displayed successively, or through some other cue such as colour of hue in a single composite image. Images are displayed on the display apparatus 17.

The detector in the preferred embodiment comprises cadmium telluride bulk single crystal. The inherent spectral resolution of the material allows the processor to resolve incident radiation intensity differentially across a plurality of pre-set frequency/energy bands in accordance with the principles of the invention.

The source 1 generates x-rays across a relatively broad spectrum of energy, so that this resolution may be exploited. It may be a plural source, or a single source with the necessary spectrum spread. The source 1 is preferably tungsten source.

In accordance with the invention, an apparatus and method is described which can offer specific material characterisation based on data which resolved spatially in two dimensions and which resolves that spatial data further spectrally.

The invention claimed is:

1. A detector apparatus for scanning of and obtaining radiation data from an object comprising:
a radiation source;
a radiation detector system spaced therefrom to define a scanning zone and to collect in use a dataset of information about radiation incident at a detector after interaction with the object in the scanning zone and adapted to resolve such collected information spatially in two dimensions across a scanning area and spectroscopically across a plurality of frequency bands in the spectrum of the source;
wherein the detector system is adapted to resolve such collected information spectroscopically in that the detector exhibits a spectroscopically variable response across at least a part of the spectrum of the source; and
wherein the detector system is adapted to resolve such collected information spatially in that it comprises:
a rastering module configured to divide the scanning area into a plurality of pixels in each of two dimensions at a plurality of resolutions; and
a detector control means to move the detector across the scanning area to scan such pixels successively and thereby collect a dataset for each pixel.

2. An apparatus in accordance with claim 1 wherein the detector system is adapted to resolve collected information spectroscopically across at least three frequency bands.

3. An apparatus in accordance with claim 1 wherein the detector system is configured to detect transmitted radiation in that the apparatus comprises a radiation source and a radiation detector system spaced therefrom to define a scanning zone in a radiation transmission path therebetween and thus collect in use a dataset of information about transmissivity of the object in the scanning zone.

4. An apparatus in accordance with claim 1 wherein the source comprises a source to deliver high-energy radiation, and the detector system is adapted correspondingly to detect radiation in the spectrum of the source.

5. An apparatus in accordance with claim 1 further comprising an image generation apparatus to generate at least a first image from an output of the detector system.

6. An apparatus in accordance with claim 5 further comprising an image display adapted to display at least the first image.

7. An apparatus in accordance with claim 5 wherein the image generation apparatus is adapted to receive intensity data from a plurality of spectroscopically resolved energy bands and display these separate datasets of intensity data as separate images successively or simultaneously.

8. An apparatus in accordance with claim 1 wherein the detector comprises a single pixel detector.

9. An apparatus in accordance with claim 1 wherein the detector system is fabricated from a material inherently capable of exhibiting a spectroscopically variable response across at least part of the spectrum of the source.

10. An apparatus in accordance with claim 9 wherein the detector comprises a semiconductor material selected from cadmium telluride, cadmium zinc telluride (CZT), cadmium manganese telluride (CMT), germanium, lanthanum bromide, thorium bromide.

11. An apparatus in accordance with claim 9 wherein the detector comprises a semiconductor material or materials formed as bulk crystal including a Group II-VI semiconductor material.

12. An apparatus in accordance with claim 11 wherein the detector comprises a semiconductor material selected from cadmium telluride, cadmium zinc telluride (CZT), cadmium manganese telluride (CMT).

13. An apparatus in accordance with claim 1 wherein the rastering module is configured to divide the scanning area into at least a coarse and a fine resolution, and is further configured to enable selection between the resolutions by a user through a suitable user input interface.

14. An apparatus in accordance with claim 1 wherein the radiation is at least of one x-rays, gamma rays, and subatomic particle radiation.

15. An apparatus in accordance with claim 1 wherein the radiation source is adapted to emit a radiation beam over a wide area, and wherein the detector has a reduced detection area that is configured to cover and differentiate across only a small part of the overall area to be scanned at any given time.

16. A method of obtaining radiation interaction data from an object comprising the steps of:
providing a radiation source and a radiation detector system spaced therefrom to define a scanning zone therebetween, wherein the detector system is adapted to resolve collected information spectroscopically in that it comprises a detector that exhibits a spectroscopically variable response across at least a part of the spectrum of the source;
defining a scanning area for collection of radiation incident at the detector;
dividing the scanning area into a plurality of pixels in each of two dimensions at a plurality of resolutions;
moving the detector across the scanning area to scan such pixels successively and thereby collect a dataset for each pixel of information about radiation incident at the detector after interaction with the object in the scanning zone; and
resolving each such dataset spectroscopically across a plurality of frequency bands within the spectrum of the source.

17. A method in accordance with claim 16 wherein the detector is adapted to differentiate information spatially to a resolution of fewer than the said number of pixels and/or is dimensioned to less than the desired scanning area of the dataset such that the spatial resolution in the collected dataset is attributable at least in part to the step of moving the detector across the scanning area to scan pixels successively in each of two dimensions at a plurality of resolutions.

18. A method in accordance with claim 17 wherein the detector is a single pixel detector, and the spatially resolved dataset is assembled by scanning each pixel individually.

19. A method in accordance with claim 16 comprising the steps of providing a radiation source and a radiation detector system spaced therefrom to define a scanning zone in a radiation transmission path therebetween, and thereby collecting a dataset of information about transmissivity of the object in the scanning zone.

20. A method in accordance with claim 16 comprising a preliminary step of scanning/imaging the object using any suitable apparatus to identify areas of interest in the object and wherein steps of claim 16 are subsequently performed to further investigate such areas of interest.

21. A method in accordance with claim 16 further comprising the step of generating an image of the object in the scanning zone.

22. A method in accordance with claim 21 further comprising the step of displaying such generated image on a suitable display apparatus.

23. A method in accordance with claim 21 wherein each collected image is resolved spectroscopically across a plurality of bands to generate an energy-differentiated composite image or succession of images.

24. A method in accordance with claim 16 performed initially at a first coarser resolution to identify areas of an object for further investigation and subsequently at a second finer resolution collecting data only from those areas.

25. A method in accordance with claim 16 wherein the radiation source is an x-ray or a gamma ray source.

26. A method in accordance with claim 16 wherein the radiation source emits a radiation beam over a wide area, and wherein the detector has a reduced detection area that covers and differentiates across only a small part of the overall area to be scanned at any given time.

* * * * *

UNITED STATES PATENT AND TRADEMARK OFFICE
CERTIFICATE OF CORRECTION

PATENT NO.       : 8,660,239 B2                                      Page 1 of 1
APPLICATION NO.  : 13/126409
DATED            : February 25, 2014
INVENTOR(S)      : Ian Radley It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 344 days.

Signed and Sealed this

Twenty-ninth Day of September, 2015

Michelle K. Lee
*Director of the United States Patent and Trademark Office*